(12) United States Patent
Roe et al.

(10) Patent No.: US 6,878,120 B2
(45) Date of Patent: Apr. 12, 2005

(54) METHODS AND APPARATUS FOR SUCTIONING AND PUMPING BODY FLUID FROM AN INCISION

(75) Inventors: Jeffrey N. Roe, San Ramon, CA (US); Joel S. Douglas, Santa Clara, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 328 days.

(21) Appl. No.: 10/118,048

(22) Filed: Apr. 8, 2002

(65) Prior Publication Data

US 2002/0111565 A1 Aug. 15, 2002

Related U.S. Application Data

(63) Continuation of application No. 09/567,054, filed on May 8, 2000, now Pat. No. 6,485,439, which is a continuation of application No. 09/066,784, filed on Apr. 28, 1998, now Pat. No. 6,086,545.

(51) Int. Cl.[7] ................................................. A61B 5/00
(52) U.S. Cl. ........................................................ 600/583
(58) Field of Search .................................. 600/573, 576, 600/583

(56) References Cited

U.S. PATENT DOCUMENTS

| | | | |
|---|---|---|---|
| 4,360,016 A | 11/1982 | Sabrine | |
| 4,503,856 A | 3/1985 | Cornell et al. | |
| 4,517,978 A | 5/1985 | Levin et al. | |
| 4,637,403 A | 1/1987 | Garcia et al. | |
| 4,653,513 A | 3/1987 | Dombrowski | |
| 4,850,973 A | 7/1989 | Jordan et al. | |
| 4,858,607 A | 8/1989 | Jordan et al. | |
| 4,869,249 A | 9/1989 | Crossman et al. | |
| 4,895,147 A | 1/1990 | Bodicky et al. | |
| 4,920,977 A | 5/1990 | Haynes | |
| 4,924,879 A | 5/1990 | O'Brien | |
| 4,976,724 A | 12/1990 | Nieto et al. | |
| 4,995,402 A | 2/1991 | Smith et al. | |
| 5,217,480 A | 6/1993 | Haber et al. | |
| 5,318,583 A | 6/1994 | Rabenau et al. | |
| 5,318,584 A | 6/1994 | Lange et al. | |
| 5,320,607 A | 6/1994 | Ishibashi | |
| 5,368,047 A | * 11/1994 | Suzuki et al. | ................ 600/578 |
| 5,387,203 A | 2/1995 | Goodrich | |
| 5,402,798 A | 4/1995 | Swierczek et al. | |
| 5,421,816 A | 6/1995 | Lipkovker | |
| 5,445,611 A | 8/1995 | Eppstein et al. | |
| 5,458,140 A | 10/1995 | Eppstein et al. | |
| 5,582,184 A | 12/1996 | Erickson et al. | |
| 5,628,764 A | 5/1997 | Schraga | |
| 5,666,966 A | 9/1997 | Horie et al. | |
| 5,871,494 A | 2/1999 | Simons et al. | |
| 6,086,545 A | 7/2000 | Roe et al. | ................ 600/570 |
| 6,485,439 B1 | 11/2002 | Roe et al. | |

FOREIGN PATENT DOCUMENTS

| | | |
|---|---|---|
| EP | 0 166 574 A2 | 1/1986 |
| EP | 0 212 906 A2 | 3/1987 |
| EP | 0 622 046 A2 | 11/1994 |
| JP | 7155310 | 12/1993 |
| WO | WO 97/42885 | 11/1997 |
| WO | WO 97/43962 | 11/1997 |

* cited by examiner

*Primary Examiner*—Eric F. Winakur
(74) *Attorney, Agent, or Firm*—Woodard, Emhardt, Moriarty, McNett & Henry LLP

(57) ABSTRACT

A sampling device for sampling body fluid includes a casing which is pressed against a skin surface to produce a seal therewith. A cocking mechanism is pulled rearwardly to place a lancing device in a cocked state. By releasing a trigger, the lancing device is driven forward to produce an incision in the skin, and then is retracted out of the incision. A plunger mounted on the cocking mechanism is then retracted to generate a negative pressure at the front end of the casing to draw body fluid from the incision.

26 Claims, 4 Drawing Sheets

METHODS AND APPARATUS FOR SUCTIONING AND PUMPING BODY FLUID FROM AN INCISION

The present application is a continuation of U.S. patent application Ser. No. 09/567,054, filed May 8, 2000, now U.S. Pat. No. 6,485,439, which is a continuation of U.S. patent application Ser. No. 09/066,784, filed Apr. 28, 1998, now U.S. Pat. No. 6,086,545, all of which are hereby incorporated by reference in their entirety.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5–50 $\mu$L. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

The centuries-old practice of cupping has survived into modern times. Cupping is a treatment in which evacuated glass cups are applied to intact skin in order to draw blood toward or through the surface. The cuppist pierces the skin and uses suction cups to draw out blood. That method was used as a therapeutic procedure for disorders associated with an excess of blood (high blood pressure, circulation problems and muscular pain), one of the four humors of medieval physiology.

A more recent application for cupping has been the withdrawal of blood from a wound for the purpose of applying the blood to a diagnostic test strip. An instrument employed for that purpose comprises an inverted cup-shaped element having a piston. After an incision has been made in the skin by a separate lancet, the piston is depressed, against the bias of a spring, and a rim of the cup-shaped element is applied against the skin in surround relationship to the incision. By then releasing the piston for extension by the spring a vacuum is created around the incision to draw a drop of blood therefrom. Such an instrument is made by Nipuro Medical Equipment K.K. in Tokyo, Japan.

A shortcoming of such an instrument is the inconvenient need for the user to manipulate two separate pieces of equipment, i.e. the lancet and the suction device.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate site, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

Cornell et al. U.S. Pat. No. 4,503,856 describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. Nos. 4,850,973 and 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

It has also been proposed to provide a skin-lancing device with a vacuum-generating device in a single housing, to enable a blood sample to be forcefully suctioned out of an incision made by the skin-lancing device. Exemplary of such devices are: Garcia et al. U.S. Pat. No. 4,637,403; Haber et al. U.S. Pat. No. 5,217,480; Suzuki et al. U.S. Pat. No. 5,368,047; Dombrowski U.S. Pat. No. 4,653,513; and Bodicky et al. U.S. Pat. No. 5,320,607. In the Bodicky et al. patent the lancet is fixed to a suction plunger which can be retracted, along with the lancet, to create a vacuum after the skin has been pierced by the lancet. The need to retract the lancet along with the plunger to create a vacuum complicates the design of the internal structure of the apparatus.

The Suzuki et al. patent discloses a suction plunger which serves not only as a vacuum generator, but also as an actuator for releasing a cocked lancet for firing.

Erickson et al. U.S. Pat. No. 5,582,184, describes a means of collecting and measuring body fluids. This system uses a coaxial hollow lancet and capillary tube disposed within a spacer member. The spacer member limits the depth of lancet penetration, and compresses body tissue around the lancet while the lancet is in the skin, for improving the flow of interstitial fluid to the incision. However, the incision may tend to close around the lancet, thereby limiting the amount of body fluid that can be obtained.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices.

U.S. Pat. Nos. 5,421,816; 5,445,611 and 5,458,140 disclose, as a replacement for invasive sampling, the use of ultrasound to act as a pump for expressing interstitial fluid directly through intact (i.e., non-lanced) skin. The amount of fluid which can be obtained by way of such non-invasive vibration is minimal, however.

The disclosures of the above patents are incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive, particularly by penetrating less sensitive areas of the skin.

Furthermore, known lancing devices include manually actuable buttons for triggering the lance-driving mechanism once the user has placed the device against his/her skin. Because the user knows the precise instant when the lancet will be triggered and pain will be felt, there is a tendency for the user to jerk or raise the device at the instant of triggering, which can lead to inconsistent skin penetration, or possibly no penetration. Therefore, a further object of the invention is to provide a lancing device which eliminates such a tendency on the part of the user.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 μL for one test device and 8 μL for another test device, as appropriate.

It is a further object of the invention to provide a device for minimally invasive sampling comprising a reusable sampler and disposable sample lancet and collection device.

SUMMARY OF THE INVENTION

The present invention relates to a sampling device for sampling body fluid. The sampling device comprises a casing defining a longitudinal axis, and a skin-lancing mechanism mounted in the casing for extending a lance through a longitudinal front end of the casing and against a skin surface to form an incision therein, and then retracting the lance back into the housing. A trigger is provided for releasably holding the skin-lancing mechanism in a cocked state. An actuator is provided for moving the trigger to a released position. A plunger is arranged separately from the actuator and is longitudinally rearwardly movable relative to both the skin-lancing mechanism and the actuator, for generating a negative pressure at the front end of the casing to draw body fluid from the incision.

The invention also relates to a method of obtaining a sample of body fluid from a body. The method employs a device comprising a casing, a skin-lancing mechanism and cocking mechanism disposed in the casing, a trigger mounted on the casing for holding the skin lancing mechanism in a cocked state, a plunger mounted on the casing for longitudinal movement relative thereto, a hollow outer ring mounted at a front longitudinal end of the casing for longitudinal movement relative thereto, the outer ring including an annular front surface for engaging a skin surface and establishing a seal therewith, and an inner ring situated coaxially within the outer ring and having a front face. The method comprises the steps of:

A. orienting the skin lancing mechanism in a cocked state;

B. positioning the front end of the outer ring against a skin surface to form a seal therewith, with the plunger held in a forward position;

C. displacing the casing forwardly to displace the outer ring rearwardly relative thereto, whereby a rear end of the outer ring releases the skin lancing mechanism from the cocked state and a spring extends a lance of the skin lancing mechanism forwardly and against the skin surface to form an incision therein and then retracts the lancing mechanism;

D. longitudinally rearwardly retracting the plunger relative to both the skin lancing mechanism and the outer ring for generating a negative pressure at the front end of the outer end to draw body fluid from the incision;

E. displacing the casing forwardly to cause the inner ring to engage the skin surface and express additional body fluid therefrom while breaking the seal between the outer ring and the skin surface;

F. removing the device from the skin surface;

G. moving the plunger forwardly; and

H. repeating steps A, B, D, and E at least once.

BRIEF DESCRIPTION OF THE DRAWING

The objects and advantages of the invention will become apparent from the following detailed description of preferred embodiments thereof in connection with the accompanying drawing in which like numerals designate like elements and in which.

DETAILED DESCRIPTION OF PREFERRED EMBODIMENTS OF THE INVENTION

Figure 1:
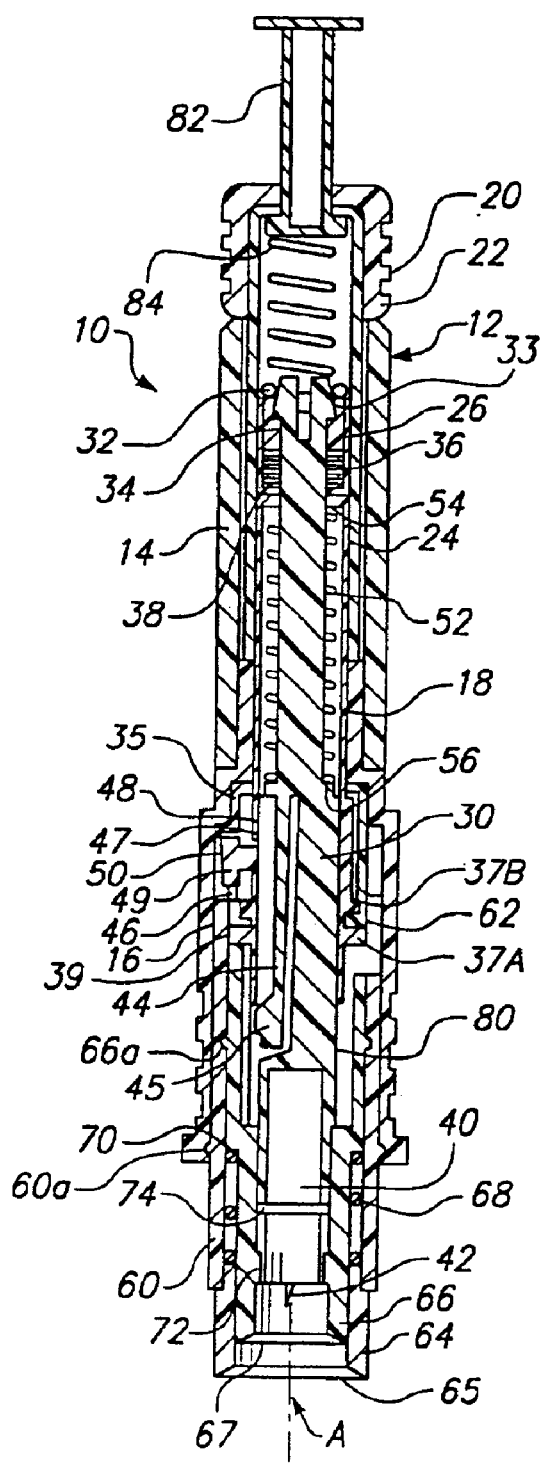
FIG. 1 is a longitudinal sectional view through a blood sampling device according to a first embodiment of the invention, with the lancet carrier in an unarmed condition.

A lancing and suctioning device 10 (see FIG. 1) according to one preferred embodiment of the invention comprises an outer housing 12 having upper and lower portions 14, 16 connected together, and an inner housing 18 fixed to the outer housing.

Mounted for vertical reciprocation in the upper portion 14 of the outer housing 12 is a cocking mechanism 20 comprising a pull handle 22 to which is fixedly secured a hollow draw tube 24. Fixed to an inner wall of the draw tube 24 is a draw ring 26.

Situated within the draw tube 24 is a skin-lancing mechanism which includes a draw bar 30 having a pair of flexible hooks 32 at its upper end. The hooks are releasably latched to a sleeve 34 which is movably disposed within the draw ring 26. A coil compression spring 36 acts between a flange 33 of the sleeve 34 and an inner flange 38 of the draw ring 26.

A trigger sleeve 35 is mounted within the lower portion 16 of the outer housing 12. A lower end of the trigger sleeve rests upon a first outer flange 37A of the inner housing, and a second outer flange 37B of the inner housing rests upon an inner projection 39 of the trigger sleeve.

At its lower end the draw bar 30 frictionally holds a skin-lancing medium in the form of a disposable lancet 40 in which a needle 42 is disposed. The draw bar 30 includes a flexible latch finger 44 that has a projection 45 adapted to be received in a hole 46 of the inner housing 18 (see FIG. 2) when the device is armed.

A trigger 49 is mounted in a hole 47 of the trigger sleeve 35 and includes an arm 48 extending partially into the hole 46. The trigger 49 includes an inclined cam follower surface 50.

A coil compression spring 52 acts between a top wall 54 of the inner housing 18 and a shoulder 56 of the draw bar.

Slidably disposed within a lower end of the lower portion of the outer housing is an actuator 60 in the form of a firing tube which includes an upper cam surface 62. Fixed to a lower end of the actuator 60 is a cylindrical outer ring 64, having an end surface 65 of generally frusto-conical shape so as to be oriented at a downward and inward inclination to generally face a longitudinal axis A of the device. The tube 60 can be yieldably mounted within the housing by means of radial detents 60a, enabling the tube 60 to be removed (in order to install a lancet 40) and then snapped back into place.

Disposed coaxially within the actuator 60 and outer stimulator ring 64 is an inner cylindrical ring 66 having a frusto-conical end surface 67 also oriented at a downward and inward inclination. The ring 66 can be retained in the actuator tube 60 by means of radial detents 66a.

The end surfaces 65 and 67 are of circular configuration when viewed along the axis A, other configurations, such as polygonal, oval, etc., are possible.

The rings 64, 66, together with the housing 12, form a casing.

A coil compression spring 68 acts between an upper end of the outer stimulator ring 64 and a downwardly facing shoulder 70 of the inner stimulator ring 66.

The inner stimulator ring 66 includes a lance stop flange 72 adapted to be engaged by a lance ring 74 of the lancet 40 as will be explained.

The first flange 37A of the inner housing rests upon a support sleeve 80 which, in turn, rests upon an upper end of the inner stimulator ring 66.

A plunger 82 is slidably mounted in the upper end of the pull handle 22 for vertical movement relative thereto. A coil compression spring 84 is mounted in the draw tube 24 and acts between an underside of the plunger 82 and a top side of the sleeve 34 to bias the plunder upwardly. As will be explained, the plunger functions to create a negative pressure within the cylindrical ring 64 when the plunger moves upwardly while the outer ring 64 is pressed against a user's skin. That is, there is sufficient looseness between the parts of the device to enable a negative pressure created within the draw tube by the plunger 82, to be transmitted to the inside of the outer ring 64.

Figure 2:
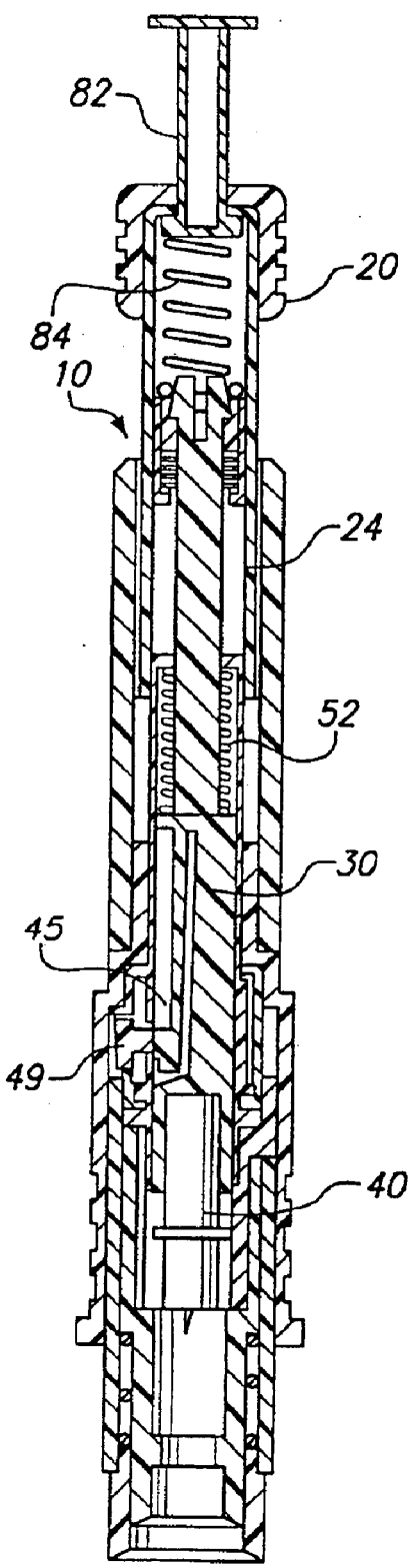
FIG. 2 is a view similar to FIG. 1, with the lancet carrier being moved to an armed condition.
Figure 3:
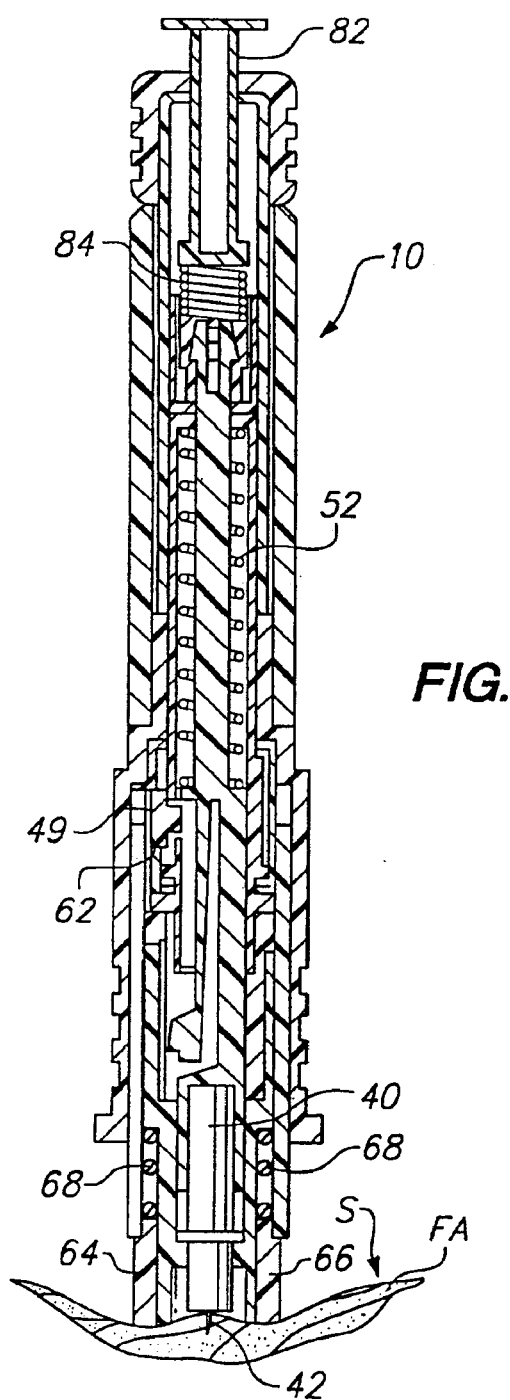
FIG. 3 is a view similar to FIG. 2 after a vacuum plunger has been depressed and the lancet carrier has been triggered to cause a lancet to penetrate the skin.

In practice, when a fluid sample, such as blood or interstitial fluid, is to be taken from a user's body, a lancing and suctioning device according to the present invention can be used to minimize pain. To do so, a region of the user's body having less sensitivity than, for example, a fingertip, is selected. Such a low-sensitivity region could be the user's forearm for example. Initially, the handle 22 is pulled up to raise the drawbar 30 until the projection 45 of the latch finger 44 snaps into the hole 46 of the inner housing 18, as shown in FIG. 2. Simultaneously, the spring 52 is compressed. Then, the user depresses the plunger 82 against the bias of the spring 84, e.g., by means of a thumb of the user's hand while the remaining fingers grip the housing 12 and press the outer stimulator ring 64 against the user's skin S, e.g., on the selected forearm region FA. Accordingly, the ring 64 and the cam surface 62 of the actuator 60 are moved upwardly to displace the trigger 49 radially inwardly, whereupon the projection 45 of the latch finger 44 is disengaged from the hole 46. Accordingly, the spring 52 expands to displace the drawbar 30 downwardly so that the needle 42 punctures the skin sufficiently deep to cut capillaries in the superficial vascular plexus, as shown in FIG. 3. Simultaneously, the spring 68 is compressed. The extent of displacement of the drawbar 30 is limited by engagement between the lance ring 74 with the lance stop 72.

Figure 4:
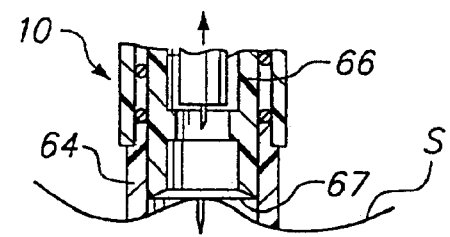
FIG. 4 is a fragmentary view similar to FIG. 1 after an incision has been formed.

Once lancing has occurred, the compressed spring 68 expands to raise the drawbar, as well as the needle 42 and inner stimulator ring 66 from the skin (see FIG. 4).

Figure 5:
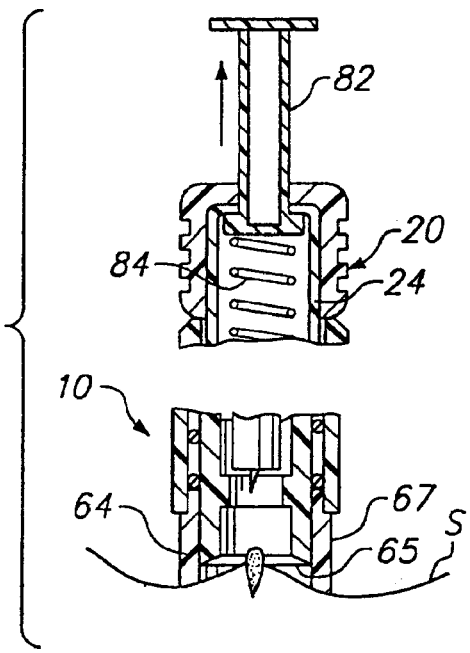
FIG. 5 is a view similar to FIG. 4 showing the vacuum plunger being retracted to generate negative pressure at the incision.
Figure 6:
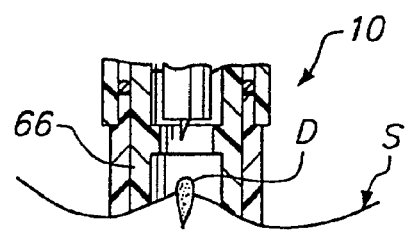
FIG. 6 is a view similar to FIG. 5 depicting an inner ring of the casing moving into contact with the skin surface to break a seal between the skin surface and an outer ring of the casing.

The user then releases the still-depressed plunger 82, whereupon the plunger is driven upwardly by the spring 84 relative to the skin-lancing mechanism 30, 40, the cocking mechanism 20, and the actuator 60 as shown in FIG. 5, to create a negative pressure within the draw tube 24. That negative pressure is transmitted down to the inside of the outer ring 64, due to the looseness between the internal parts of the device. That negative pressure bubbles or puckers the skin, thus opening the incision and forcefully drawing a drop of blood D from the wound, as shown in FIG. 6.

Then, the user can depress the housing 12 toward the user's skin, causing the outer ring 64 to be retracted against the bias of the spring 68, and allowing the end surface 67 of the inner ring 66 to contact and depress the skin away from the end surface 65 of the outer ring 64, expressing more blood from the wound and breaking the seal therebetween. Accordingly, the device can be easily and painlessly removed from the user's skin, allowing more blood to flow toward the incision. By repeatedly performing the vacuum and pumping actions over the same incision, the user is able to extract a desired sample amount from the incision.

It will thus be appreciated that the present invention enables an ample supply of blood, interstitial fluid or other body fluid to be obtained relatively painlessly from areas of the body which typically possess lesser amounts of such fluid as compared with the highly sensitive fingertip region.

Figure 7:
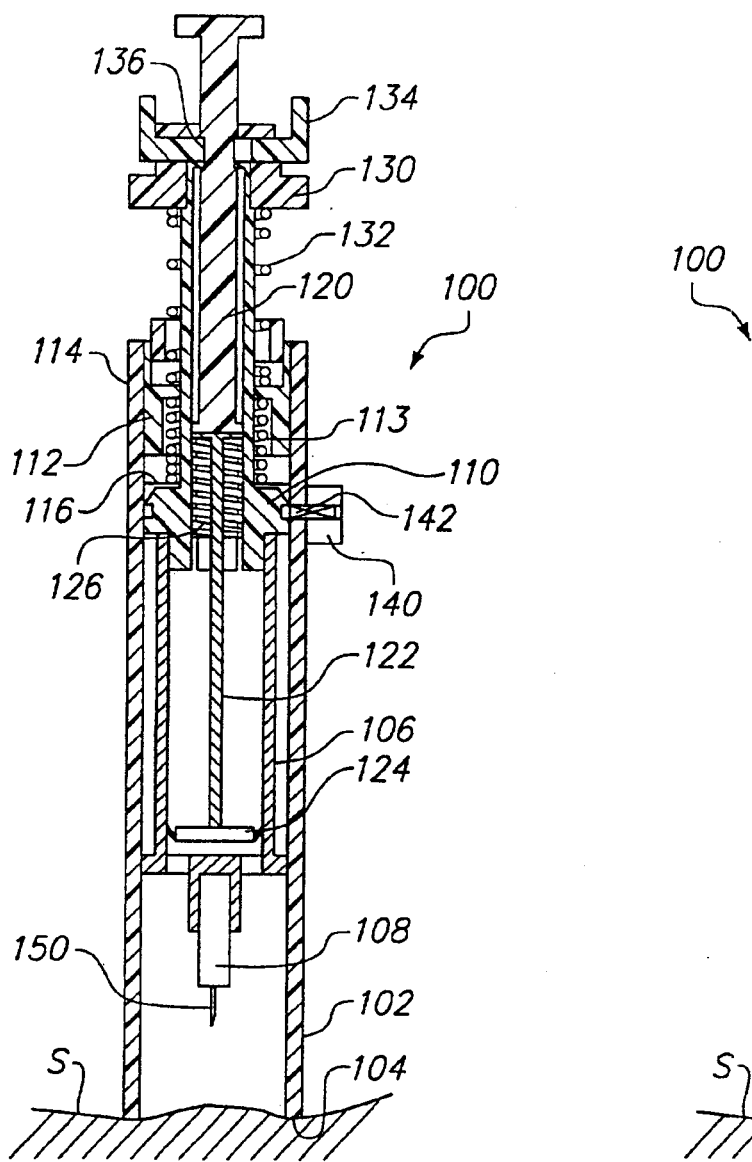
FIG. 7 is a longitudinal sectional view taken through a second embodiment of the invention, with a lancet carrier in an armed condition.
Figure 8:
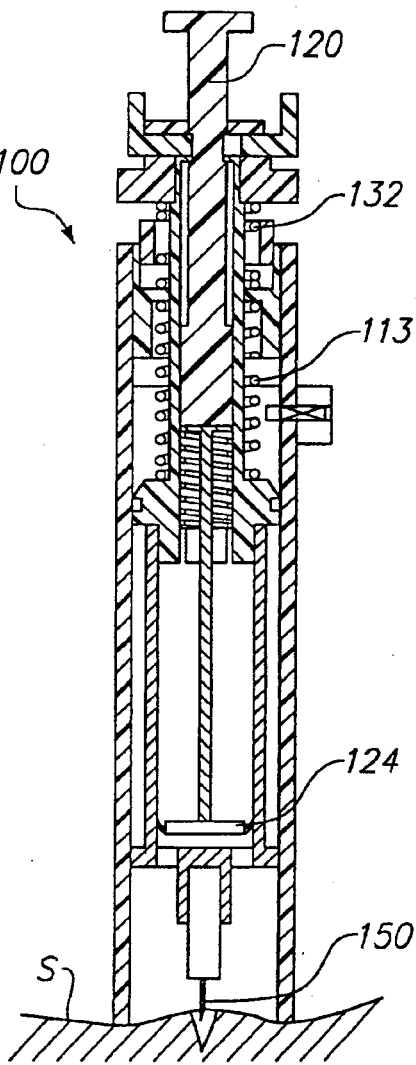
FIG. 8 is a view similar to FIG. 7 after the lance carrier has been released and a lance is in the process of forming in incision in a skin surface.
Figure 9:
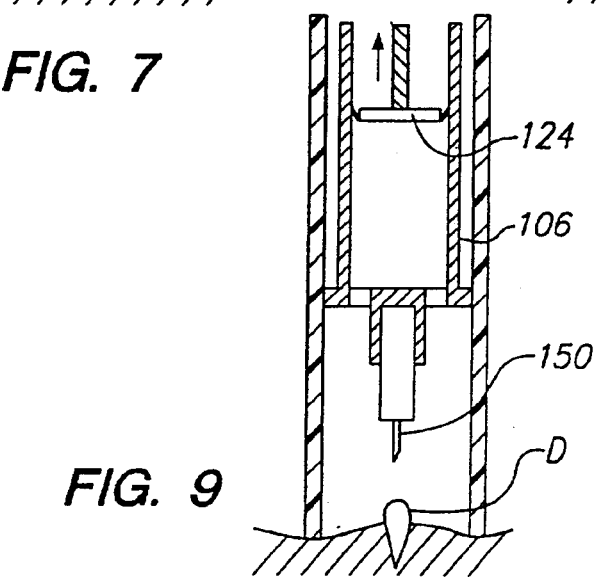
FIG. 9 is a fragmentary view of a front end of the casing as a vacuum plunger is being retracted to form a negative pressure at the incision.

A second embodiment of the invention is depicted in FIGS. 7–9. Depicted therein is a lancing and suction device 100 which includes a cylindrical casing 102 having a front face 104 for engaging a skin surface 5. A lancing mechanism mounted in the casing 102 includes a cylindrical sleeve 106 carrying a lancing element 108 at its lower end. Connected to the lancing mechanism is a cocking mechanism which includes a drawbar 110 that is screw threaded to an upper end of the sleeve 106. The drawbar 110 passes through an end wall 112 that is screw threaded in a rear end of the casing 102. A coil compression spring 113 is arranged coaxially within the casing and acts against a forwardly facing surface 114 of the end wall 112 and a rearwardly facing surface 116 of the drawbar 110 to bias the drawbar forwardly.

Mounted in the drawbar 110 for longitudinal sliding movement relative thereto is a plunger 120. Affixed to the plunger 120 and projecting forwardly therefrom is a piston rod 122 which terminates forwardly in a piston 124 situated in the sleeve 106.

A coil compression spring 126 acts between a forwardly facing surface of the piston rod 122 and a rearwardly facing surface of the drawbar to bias the piston 124 rearwardly relative to the sleeve.

Mounted on a rear end of the drawbar 110 is a collar 130. A coil compression spring 1 32 acts between a rearwardly facing surface of the drawbar 110 and a forwardly facing surface of the collar to bias the plunger rearwardly.

Mounted in the collar 130 for transverse sliding movement relative thereto is a latch 134. The latch is configured to releasably engage a notch 136 formed in the plunger 120 to retain the plunger in a forward position.

A trigger 140 is mounted in the casing 102 and carries a locking pin 142. The trigger is movably transversely relative to the casing and is spring biased inwardly so that the pin 142 can engage a recess formed in the drawbar when the drawbar is in a rearwardly retracted, cocked state.

In operation, the drawbar 110 is retracted rearwardly against the bias of spring 113 until the pin 142 enters the recess therein to retain the drawbar, sleeve 106 and lancing element 108 in a cocked state. The plunger 120 is pushed forwardly against the bias of spring 126 until the latch 134 engages the notch 136 in the plunger to retain the plunger 120 and piston 124 in a forward state.

The front face 104 of the casing 102 is pressed against a skin surface S to form a seal therewith, as shown in FIG. 7. Then, the trigger 140 is pulled out, enabling the spring 113 to drive the drawbar 110 and lancing element 108 forwardly whereby a needle 150 of the lancing element travels out of the casing to make an incision in the skin surface S as shown in FIG. 8. Then, the now-compressed spring retracts the drawbar and lancing element rearwardly, whereby the needle 150 re-enters the casing.

At this point the latch 134 is actuated to release the plunger 120 which is driven rearwardly by the spring 126. The piston 124 is also driven rearwardly to produce a negative pressure at the front end of the casing to draw a drop D of body fluid from the incision, as shown in FIG. 9. By then moving the plunger 120 forwardly, the suction is broken to enable the casing to be separated from the skin surface. The drop D of body fluid can then be sampled.

Figure 10:
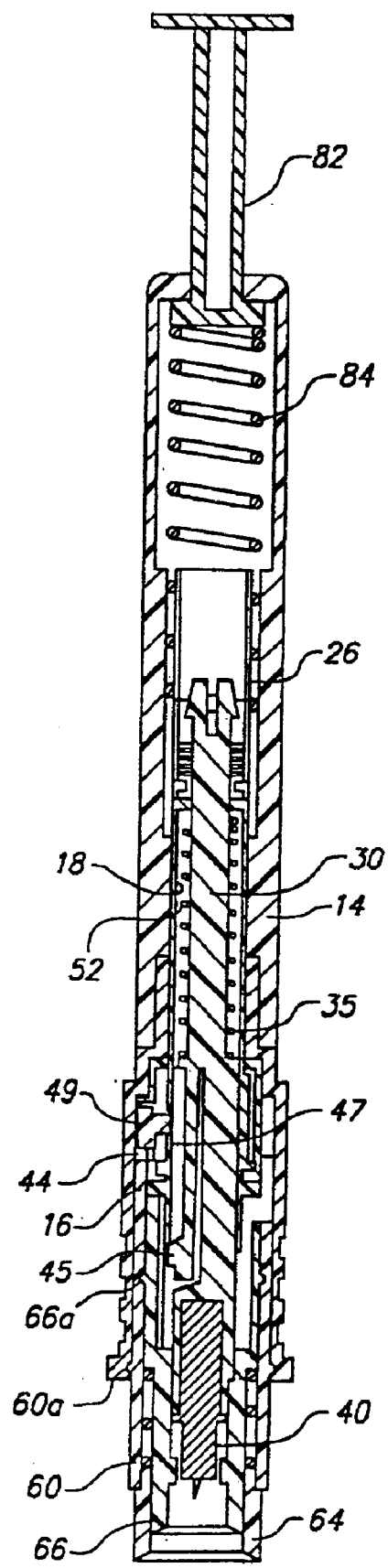
FIG. 10 is a longitudinal section view of a third embodiment of the invention.

Another embodiment of the invention is depicted in FIG. 10. That embodiment is similar to the one disclosed in connection with FIGS. 1–6, except that no cocking handle 22 is provided. Rather, cocking occurs during insertion of the lancet 40.

The same reference numerals used in FIG. 1 will be used in FIG. 10 to designate the same parts. When the actuator tube 60 is removed, the lower end of the draw bar 30 is exposed for accommodating the removal and/or insertion of a lancet 40. During the insertion of the lancet, a rearward force is applied thereto in order to displace the draw bar 30 sufficiently rearwardly to enable the projection 45 of the latch finger 44 to enter the hole 47, and thus be held therein in a cocked state. This eliminates the need for a separate cocking handle 22.

Before an incision is made, the plunger 82 is pushed forwardly. After the incision has been made (i.e., by causing the actuator 60 to move rearwardly and actuate the trigger 49), the plunger 82 is released, whereupon the spring 84 displaces the plunger rearwardly to create a negative pressure in the draw tube 24 which is transmitted forwardly to the inside of the outer ring 64 as described earlier in connection with FIG. 1.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed:

1. A sampling device for sampling body fluid, comprising:
   a casing defining a longitudinal axis;
   a skin-lancing mechanism for extending a lancet through a longitudinal front end of the casing and against a skin surface to form an incision therein, and then retracting the lancet back into the casing;
   a plunger being longitudinally rearwardly movable relative to the skin lancing mechanism, the plunger being constructed and arranged with the sampling device such that a negative pressure is generated at the front end of the casing by movement of the plunger away from the front end of the casing, the negative pressure acting to draw body fluid from the incision;
   means for driving the plunger rearwardly relative to the skin-lancing mechanism; and
   a latch constructed and arranged to release the plunger such that the plunger is rearwardly driven relative to the skin-lancing mechanism.

2. The device of claim 1, wherein the means for driving the plunger includes a spring.

3. The device of claim 2, wherein the spring is coupled to the plunger.

4. The device of claim 1, wherein:
   the plunger defines a notch; and
   the latch releasably engages the notch in the plunger to retain the plunger in a longitudinally forward state.

5. The device of claim 1, further comprising:
- a cocking mechanism coupled to the skin-lancing mechanism for positioning the skin-lancing mechanism in a cocked state; and
- wherein the plunger is longitudinally rearwardly movable relative to the cocking mechanism.

6. The device of claim 5, wherein the cocking mechanism includes a handle to manually position the skin-lancing mechanism in the cocked state.

7. The device of claim 5, wherein the cocking mechanism includes the latch adapted to be releasably latched through insertion of the lancet into the casing.

8. The device of claim 1, further comprising a trigger to releasably hold the skin-lancing mechanism in a cocked state.

9. The device of claim 8, further comprising an actuator to release the skin-lancing mechanism from the trigger.

10. A bodily fluid sampling device, comprising:
- a casing defining an opening;
- a skin-lancing mechanism disposed in the casing to extend a lancet from the opening of the casing to form an incision in skin;
- a plunger disposed in the casing, the plunger being independently moveable with respect to the skin-lancing mechanism to reduce pressure at the opening to draw bodily fluid from the incision; and
- a hollow member mounted around the opening in the casing, the hollow member having a skin engaging surface to establish a seal with the skin; and
- an inner member positioned inside the hollow member, the inner member being movable relative to the hollow member to break the seal with the skin.

11. The device of claim 10, further comprising means for moving the plunger relative to the skin-lancing mechanism.

12. The device of claim 11, wherein the means for moving the plunger includes a spring.

13. The device of claim 11, further comprising a latch constructed and arranged to release the plunger such that the plunger is moved relative to the skin-lancing mechanism by the means for moving the plunger.

14. The device of claim 10, further comprising a spring coupled to the plunger to move the plunger relative to the skin-lancing mechanism.

15. The device of claim 10, further comprising:
- a cocking mechanism coupled to the skin-lancing mechanism for positioning the skin-lancing mechanism in a cocked state; and
- wherein the plunger is independently moveable with respect to the cocking mechanism.

16. The device of claim 10, further comprising a trigger to releasably hold the skin-lancing mechanism in a cocked state.

17. The device of claim 16, further comprising:
- an actuator to release the skin-lancing mechanism from the trigger; and
- wherein the plunger is independently moveable with respect to the actuator.

18. A sampling device for sampling body fluid, comprising:
- a casing defining a longitudinal axis;
- a skin-lancing mechanism for extending a lancet through a longitudinal front end of the casing and against a skin surface to form an incision therein, and then retracting the lancet back into the casing;
- a plunger being longitudinally rearwardly movable relative to the skin lancing mechanism, the plunger being constructed and arranged with the sampling device such that a negative pressure is generated at the front end of the casing by movement of the plunger away from the front end of the casing, the negative pressure acting to draw body fluid from the incision;
- a cocking mechanism coupled to the skin-lancing mechanism for positioning the skin-lancing mechanism in a cocked state;
- wherein the plunger is longitudinally rearwardly movable relative to the cocking mechanism; and
- wherein the cocking mechanism includes a handle to manually position the skin-lancing mechanism in the cocked state.

19. A bodily fluid sampling device, comprising:
- a casing defining an opening;
- a skin-lancing mechanism disposed in the casing to extend a lancet from the opening of the casing to form an incision in skin;
- a plunger disposed in the casing, the plunger being independently moveable with respect to the skin-lancing mechanism to reduce pressure at the opening to draw bodily fluid from the incision;
- means for moving the plunger relative to the skin-lancing mechanism; and
- a latch constructed and arranged to release the plunger such that the plunger is moved relative to the skin-lancing mechanism by the means for moving the plunger.

20. A bodily fluid sampling device, comprising:
- a casing defining an opening;
- means for forming an incision in skin through the opening;
- means for reducing pressure at the opening to draw bodily fluid from the incision;
- an outer member having an end surface proximal the opening to establish a seal with the skin; and
- an inner member positioned inside the outer member, the inner member being movable relative to the outer member to break the seal with the skin.

21. The device of claim 20, wherein the means for forming the incision includes a lancet.

22. The device of claim 20, wherein the means for reducing pressure includes a plunger.

23. The device of claim 20, wherein the outer member is ring-shaped.

24. The device of claim 20, wherein the inner member is ring-shaped.

25. The device of claim 20, wherein the end surface has a generally frusto-conical shape.

26. The device of claim 25, wherein the inner member has an end surface that has a generally frusto-conical shape.

* * * * *